United States Patent [19]
Carr et al.

[11] Patent Number: 5,691,465
[45] Date of Patent: Nov. 25, 1997

[54] MULTI-PLATE THIN FILM CARBON MONOXIDE SENSOR

[75] Inventors: Richard A. Carr, Rowlett; Kirk S. Laney, Plano, both of Tex.

[73] Assignee: Texas Instruments Incorporated, Dallas, Tex.

[21] Appl. No.: 693,766

[22] Filed: Aug. 7, 1996

Related U.S. Application Data

[60] Provisional application No. 60/001,943, Aug. 7, 1995.
[51] Int. Cl.[6] .................................................. G01N 21/59
[52] U.S. Cl. .......................... 73/24.02; 356/437; 422/91; 436/167
[58] Field of Search ........................... 73/23.2, 23.31, 73/24.02, 335.01, 31.02, 31.01, 31.05; 356/409, 437, 438; 422/86, 91, 88; 436/164, 167, 169, 170

[56] References Cited

U.S. PATENT DOCUMENTS 4,661,320  4/1987  Ito et al. ............................ 422/88 X
4,668,635  5/1987  Forster ............................... 422/88 X
5,405,583  4/1995  Goswami et al. .................... 422/86
5,494,640  2/1996  Simon et al. ...................... 436/167 X Primary Examiner—Michael Brock
Attorney, Agent, or Firm—Alan K. Stewart; Wade James Brady, III; Richard L. Donaldson

[57] ABSTRACT

A gas detector, preferably for carbon monoxide detection, which includes a light detector(5), a light source (1) for providing a light beam which travels along a light path to the detector and detection chemistry (3) disposed in the light path for altering the light beam responsive to the impingement of a predetermined gas thereon. The detection chemistry includes a plurality of spaced apart members, each disposed in the light path. Each member includes a chemistry responsive to the impingement of the predetermined gas thereon for reversibly altering the light transmissive properties of the detection chemistry. The chemistry of any one of the members can differ from the chemistry of one or more of the other members if more than two members are present. The detection chemistry can, in part, act as a filter to light from the light beam. The detection chemistry is disposed in a gas ambient, the gas ambient being disposed between the spaced apart members.

7 Claims, 1 Drawing Sheet

MULTI-PLATE THIN FILM CARBON MONOXIDE SENSOR

This application claims priority under 35 USC § 119(e)(1) of provisional application No. 60/001,943, filed Aug. 7, 1995.

BACKGROUND OF THE INVENTION

1. Field of the Invention

This invention relates to a sensor for detecting carbon monoxide.

2. Brief Description of the Prior Art

Carbon monoxide sensors, in general, are well known in the prior art. Several methods of carbon monoxide detection for the purpose of personal safety are also known in the prior art. One such method uses light from a light source, such as a light emitting diode (LED) and reflects the light off of the surface of a detection chemistry and then onto a light detector. As the detection chemistry is exposed to carbon monoxide, the chemical reaction between the carbon monoxide and the detection chemistry changes a property of the detection chemistry, such as, for example, color or the optical index, and a different color is transmitted through or more or less of the light is absorbed into the detection chemistry, causing less or more light to impinge upon the detector.

A second such method is to detect the change in the light transmissivity of a detection chemistry which, when exposed to the carbon monoxide, changes its light transmissivity in a known and repeatable manner due to the presence of the carbon monoxide. In systems of this type, light from a light source, such as a light emitting diode (LED), passes directly through the chemistry and impinges upon the surface of a light detector. The frequency of the emitted light is tailored to the detection chemistry involved and can be visible light or invisible light, such as, for example, infrared. As the detection chemistry is exposed to carbon monoxide, the resulting chemical reaction changes the optical index of the detection chemistry, resulting in a change, generally a reduction, in the amount of light transmitted from the light source to the light detector.

Certain factors are involved in obtaining a resolvable signal, one of which is the thickness of the chemistry. The thicker the chemistry, the more resolvable the signal. When the detection chemistry is removed from the presence of the carbon monoxide or vice versa, the chemical reaction reverses, returning the detection chemistry to its original condition and original transmissivity. The time required for the detection chemistry to return to ambient depends upon the thickness of the detection chemistry involved. The detection chemistries utilized display hysteresis and therefore do not return to their quiescent state rapidly and therefore are not immediately available for renewed detection. This has resulted in problems for users because it is desirable to have a thick detection chemistry so that small changes and/or amounts of ambient carbon monoxide can be detected. The result has been an undesirable tradeoff between detection chemistry thickness and detection chemistry reversal to its initial or ambient (carbon monoxide-free) quiescent state. Also, due to the hysteresis in the detection chemistry, there are occasional false alarms.

SUMMARY OF THE INVENTION

In accordance with the present invention, the above described problems of the prior art in accordance with the described second method are minimized and there is provided a gas detector, principally but not exclusively for carbon monoxide detection having the properties of thick detection chemistry with concomitant relatively rapid detection chemistry reversal upon removal of the carbon monoxide from the detection chemistry of the sensor.

Briefly, the above is accomplished by slicing the detection chemistry into a plurality of thin slices or providing the thin slices initially and stacking the slices with some spacing between slices between the light source and the light detector so that the light path passes through the slices and ambient environment can pass in the space between the slices. The thin slices are provided, for example, by depositing the detection chemistry onto thin glass substrates. A second method of providing the thin slices is to impregnate medium to high density mesh screen material cut into single disks or squares. Another method is to impregnate a strip of mesh screen material and then fold the material in the manner of an accordion. Still another method is to coat plural thin clear plastic substrates with the detection chemistry. A still further method is to coat thin alumina substrates with the detection chemistry. Either one side or both sides of a substrate can be coated with the same or different detection chemistry. The detection chemistry can vary from one side of a substrate to the other side or from substrate to substrate or slice to slice to provide multiple chemistries capable of detecting plural gases.

In the case where a plurality of thin substrates is coated with the detection chemistry, an inexpensive cylindrical housing with slots therein is provided to hold several of the substrates. The cylinder has openings in both ends to allow light transmission therethrough. The number of substrates in the holder determines the amount of signal change resulting from exposure to carbon monoxide or other gas. Further, the housing can be vented at the sides thereof to allow free flow of carbon monoxide and ambient environment in and out of the housing for interaction with the detection chemistry.

A further advantage of using plural slices is that the detection chemistry on each slice and/or on opposing surfaces of any slice can be varied from the chemistry on other slices and/or surfaces. In this way, the total detection and/or other chemistry can be tailored to any specific requirements that may arise for selectivity (such as selectivity to specific materials as opposed to other materials that can be present in the environment, e.g. an ammonia block) transmission and/or isolation or to plural gases.

Detection chemistries that can be used for CO detection, with or without a block, such as, for example, an ammonia block, as well as for detection of gases other than CO, with or without a block, such as, for example, hydrocarbons, acetone, etc. are well known.

In addition, though the disclosure herein is directed to carbon monoxide detection, it should be understood that the principles herein would be applicable to detection of other materials which cause a reversible change in optical properties of a detection chemistry.

DESCRIPTION OF THE PREFERRED EMBODIMENT

Figure 1:
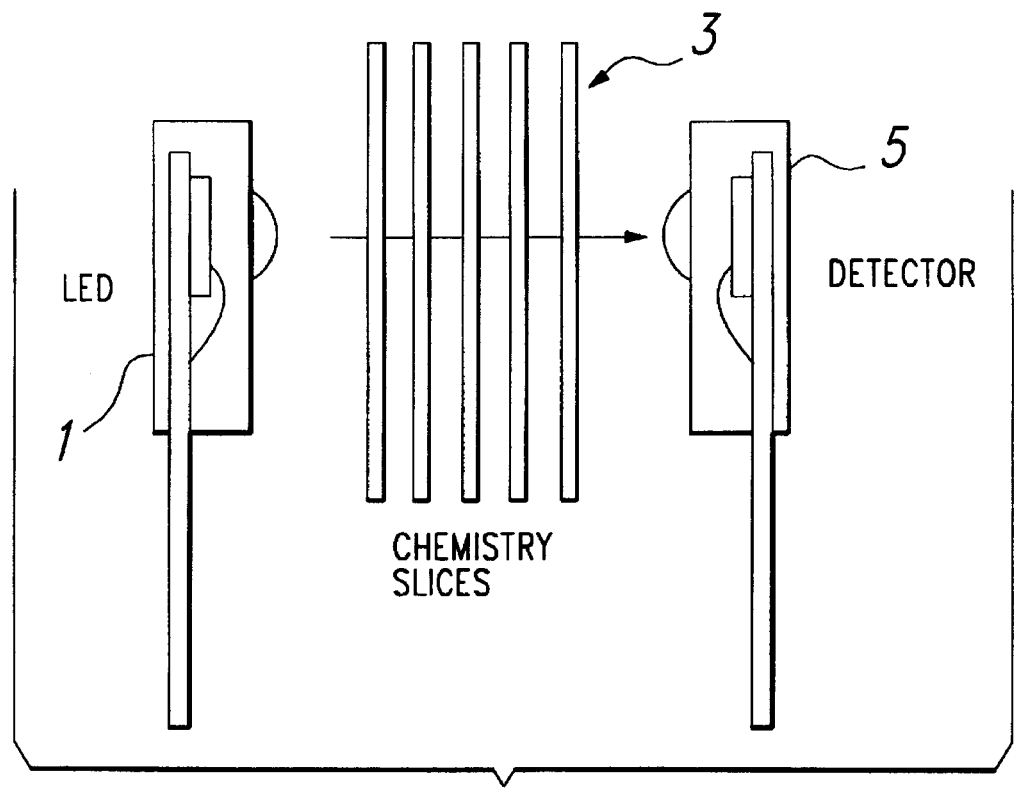
FIG. 1 is a schematic diagram of a carbon monoxide sensor in accordance with the present invention.
Figure 2:
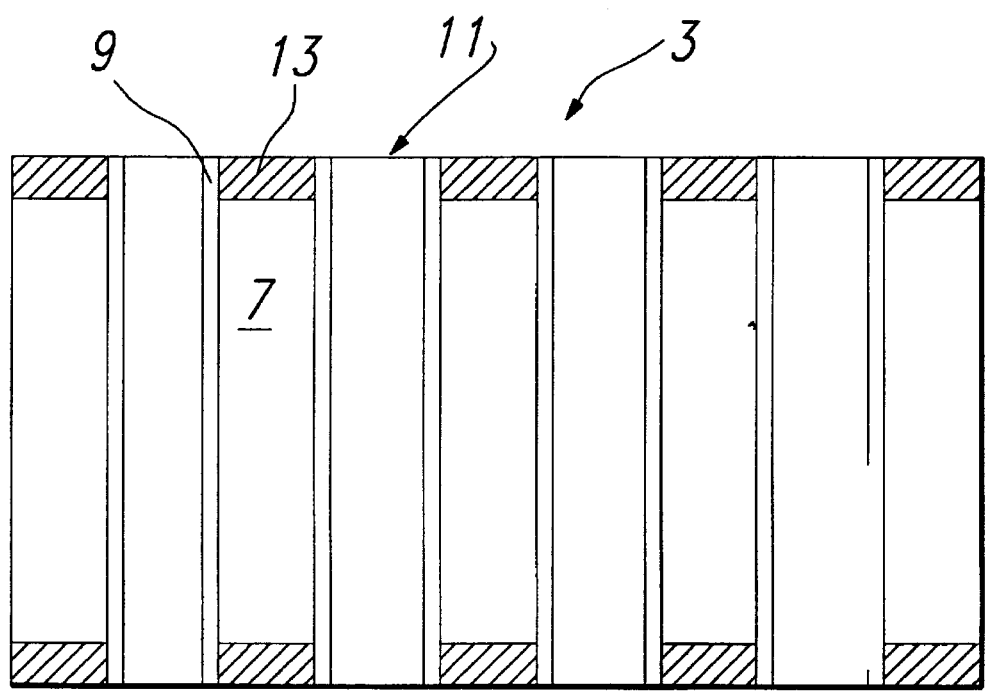
FIG. 2 is a cross-sectional view of a preferred embodiment of the chemistry 3 of FIG. 1.

Referring to FIG. 1, there is shown a carbon monoxide detector in accordance with the present invention. The detector includes a light source in the form of an LED 1, a light detector 5 and the involved detection chemistry 3 disposed in the light path between the light source and the light detector. The detection chemistry 3, as better shown in FIG. 2, comprises a plurality of spaced apart sheets 7 of rigid clear plastic having a layer of a standard CO detection chemistry material 9 on one or both surfaces of each of the sheets. The material 9 is one of many well known CO materials which undergoes a change in chemistry with exposure to carbon monoxide. The sheets 7 can be rectangular or circular and are disposed within a housing 11. Spacers 13 within the housing separate the sheets 7 from each other to provide a space between the sheets. Openings (not shown) can be provided in the housing in the regions between the sheets 7 to facilitate the entry of ambient carbon monoxide into the housing and between the sheets 7. The number of sheets 7 required within the housing is not critical and is a function of the intensity of the light source 1, the thickness of the material 9 on the sheets 7 and the transmissivity of the sheets.

It can be seen that, upon removal of the ambient carbon monoxide and because the amount of detection chemistry surface area available per unit volume is far greater than in the prior art, the carbon monoxide that had entered the detection chemistry will now be removed therefrom much more rapidly than in the prior art.

As an alternate embodiment which is not shown, the detector can have two separate light channels, one being a sense channel and one being a reference channel. In this way, normal ambient conditions can be filtered out from the sensed conditions to provide an even more accurate reading of the detected conditions.

Though the invention has been described with reference to specific preferred embodiments thereof, many variations and modifications will immediately become apparent to those skilled in the art. It is therefore the intention that the appended claims be interpreted as broadly as possible in view of the prior art to include all such variations and modifications.

We claim:

1. A gas detector which comprises:

(a) a light detector;

(b) a light source for providing a light beam which travels along a light path to said detector; and (c) detection means disposed in said light path for altering said light beam responsive to the impingement of a predetermined gas thereon, said detection means including:

(i) a plurality of spaced apart members, each of said members disposed in said light path;

(ii) each of said members including a chemistry responsive to said impingement of said predetermined gas thereon for reversibly altering the light transmissive properties of said chemistry, said chemistry of one of said members differs from the chemistry of a second of said members.

2. The detector of claim 1 wherein said gas is carbon monoxide.

3. The detector of claim 2 wherein said detection means is disposed in a gas ambient, said gas ambient being disposed between said spaced apart members.

4. The detector of claim 1 wherein one of said chemistry of one of said members acts as a filter to light from said light beam.

5. The detector of claim 4 wherein said detection means is disposed in a gas ambient, said gas ambient being disposed between said spaced apart members.

6. The detector of claim 1 wherein said detection means is disposed in a gas ambient, said gas ambient being disposed between said spaced apart members.

7. The detector of claim 1 wherein said one of said members and said second of said members are responsive to different gases.

* * * * *